United States Patent [19]

Hanifl

[11] 4,375,849

[45] Mar. 8, 1983

[54] SYRINGE NEEDLE REMOVAL AND DISPOSAL DEVICE

[75] Inventor: Paul H. Hanifl, Barrington, Ill.

[73] Assignee: Sage Products, Inc., Cary, Ill.

[21] Appl. No.: 264,541

[22] Filed: May 15, 1981

[51] Int. Cl.³ ............... B65D 25/00; B65F 7/00; B65F 1/02

[52] U.S. Cl. ............... 206/366; 206/63.5; 220/307

[58] Field of Search ............... 206/365, 366, 63.5; 229/7 SC; 220/307

[56] References Cited

U.S. PATENT DOCUMENTS

| | | | |
|---|---|---|---|
| 619,188 | 2/1899 | Kirkwood | 206/63.5 |
| 1,088,962 | 3/1914 | Bostwick | 206/63.5 |
| 1,394,391 | 10/1921 | Woolsey | 206/63.5 |
| 2,136,795 | 11/1938 | Hoffman | 229/7 SC |
| 3,095,995 | 7/1963 | Foster | 220/307 |
| 3,878,067 | 4/1975 | Schwarz | 206/366 |

FOREIGN PATENT DOCUMENTS

| | | | |
|---|---|---|---|
| 2740335 | 3/1979 | Fed. Rep. of Germany | 206/366 |
| 2040268 | 8/1980 | United Kingdom | 206/366 |

*Primary Examiner*—William T. Dixson, Jr.
*Attorney, Agent, or Firm*—Lee, Smith & Jager

[57] ABSTRACT

A syringe needle removal and disposal device is disclosed and comprises cap means and a container. The cap means includes means for disengaging needles affixed to syringes and disposing used needles into the storage container. The cap means also includes movable closure means for controlling access to the storage container. The device is portable and ensures safe disposal of used needles for hypodermic syringe needles of the one ended variety, and blood sampling needles for both the one-ended and double-ended types.

18 Claims, 7 Drawing Figures

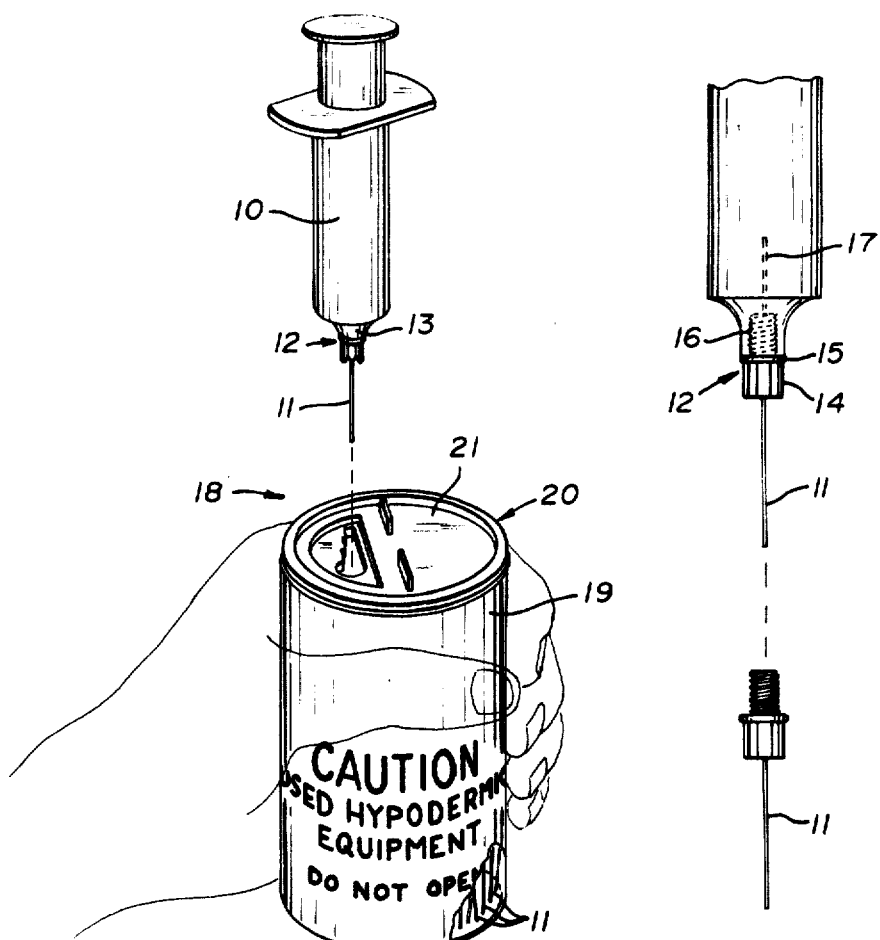
Fig. 1
Fig. 2
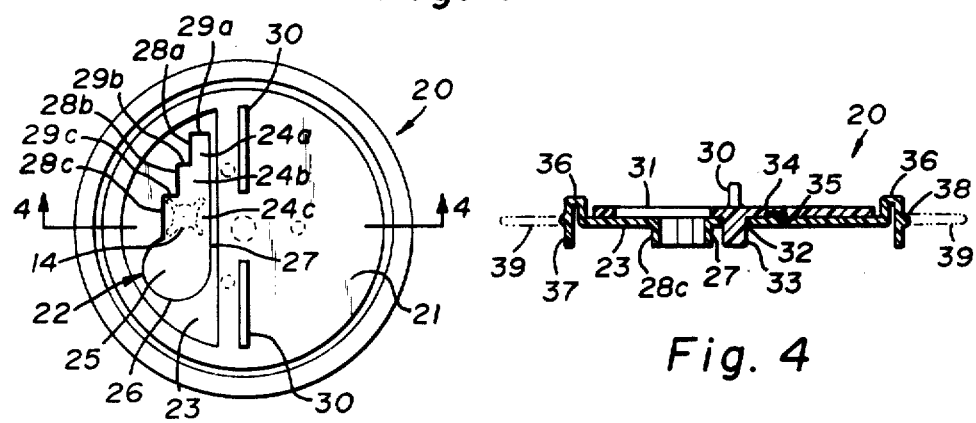
Fig. 3
Fig. 4

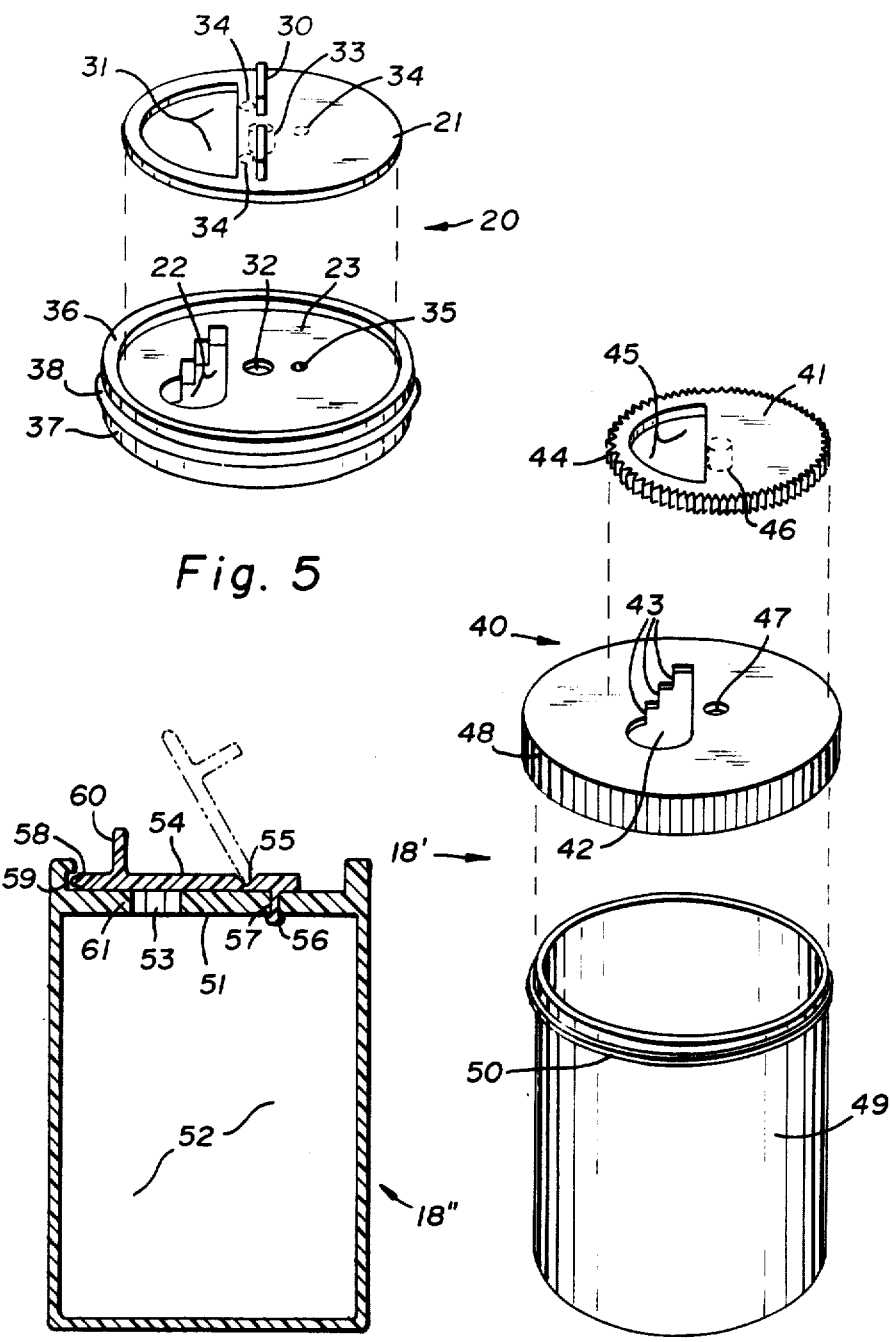

SYRINGE NEEDLE REMOVAL AND DISPOSAL DEVICE

BACKGROUND AND SUMMARY OF THE INVENTION

The invention relates to removing and disposing of needles from syringe bodies where the needle is detachable from the syringe body and would otherwise require manual manipulation for removal after use.

A great concern to hospital staff personnel, particularly medical technicians, is quick and safe disposal of needles after injection or blood sampling. When manual disposition is required the chance for skin puncturing and scratching from the sharp end of a cannular needle occurs all too often. In fact, needle accidents sustained in this manner are among the most frequent causes of injury to hospital workers. Such injuries also are the source of potential infections to the hospital personnel. It would accordingly be desirable for medical personnel to be able to dispose of these items safely and easily.

A wide assortment of devices has been provided through the years to make disposal techniques safe and fast. Many involve mere needle removal from a syringe body and others include needle severance to ensure that no re-use occurs. Yet another variety destroys the syringe as well as the needle for particular application with hypodermic syringes used for injections. However, needle destruction for double-ended blood needles would still leave the problem of what to do with the other, intact, end. Double-ended needles, usually are detachable at the needle hub, so that after taking a blood sample, the sample contained in a collection tube may be taken for laboratory testing minus the needle. Many one-ended needles are also detachable. It would be very beneficial to provide one device which can safely remove and contain detachable needles and have the additional capacity of accommodating a wide range of needle sizes. And it would be of additional significance to facilitate the detachment of both thread engaged and friction-fit needle hubs from syringe bodies.

One previous solution affords removal of friction-fit one-ended needles by the insertion of the needle through an opening into a collection box. The head, or hub, of the needle is caught behind a cover plate and pulling on the syringe body detaches the needle. No provision for removing threaded hubs is found and the device is not suited for double-end needle removal.

The prominent significance of the device disclosed is that both hypodermic injection syringe needles and single and double-ended sampling needles, which are thread engaged to a syringe body, may be quickly and safely removed and disposed of by a simple unwinding of threaded hubs from syringe bodies. The additional benefit of removal of friction-fit needles is also obtained.

It is also important in today's climate of increased medical costs to provide a disposable unit which may be simply manufactured out of inexpensive material but yet offer containment for a large number of used, or contaminated needles. The present invention satisfies such a need. The invention further provides a movable lid for closure of the storage container. The lid permits safe transportation to a refuse disposal, and portability for carrying on the person from patient to patient.

BRIEF DESCRIPTION OF THE DRAWING

FIG. 1 is a perspective view of the hand-held needle removal and disposal device in accordance with one embodiment for practicing the invention and including a typical syringe and needle poised for needle removal and disposal;

FIG. 2 is a an exploded and enlarged view of the typical syringe and needle as shown in FIG. 1;

FIG. 3 is a top view of the removal and disposal device shown in an open position ready for removal of a needle, and showing in phantom lines a needle hub collar in an engaged position;

FIG. 4 is a cross-sectional view of FIG. 3 taken along line 4—4 and looking in the direction of the arrows;

FIG. 5 is a perspective exploded view of the cap means of the removal and disposal device as shown in FIG. 1;

FIG. 6 is an alternate embodiment of the invention shown in exploded perspective view; and FIG. 7 is another alternate embodiment of the invention, shown in cross-section, and having the cap means and storage container integrally formed.

DESCRIPTION OF THE ILLUSTRATED EMBODIMENTS

FIGS. 1-5 illustrate an example of one embodiment for the invention and FIGS. 6 and 7 show alternate conformations within the scope of the invention. It will be appreciated that the removal and disposal device of the invention may be hand-held for portability on the person during the course of the day as injections or blood samples are conducted from patient to patient. Not only is removal of detachable needles attained easily and safely, but storage is provided for the used needles in a manner that allows a large number of used needles to be collected before ultimate disposal.

FIGS. 1 and 2 depict the removal and disposal operation for a syringe 10 having a conventional one-ended design and also shown, in phantom, a double-ended needle configuration equally removed and disposed by the invention. For purposes of illustration it will be seen that syringe 10 includes a cannular needle 11 having a hub 12 detachably engaged within ferrule 13 of the syringe. Hub 12 includes a flanged collar 14 integral with a base 15, which is provided to abut ferrule 13 while the needle is engaged in the syringe. Attachment within ferrule 13 is afforded by means of a threaded portion 16 extending from the other side of base 15. Another detachable configuration could include an unthreaded portion, instead of threaded the portion 16, on the hub 12. A friction-fit of the hub 12 within ferrule 13 would allow the needle to be removed by a simple pulling action rather than by unthreading. As seen in phantom in FIG. 2, cannular needle 11 may extend through hub 12 to include a second needle end 17. That design is useful for blood sampling needles where the second end 17 is provided to pierce a resilient sealing stopper at the end of a collection tube, well known to the medical industry.

Syringe 10 is shown in FIG. 1 poised ready for entry and removal operations above removal and disposal device 18. Device 18 includes a collection and storage container 19 having an open upper end wherein cap means 20 is securely fitted. Cap means 20 affords removal of cannular needle 11 and access thereto is controlled by a closure means such as movable closure lid 21.

With attention now turned to FIGS. 3 and 4, the significant advantages provided by the invention are shown in closer detail with respect to cap means 20.

The objectives attained include quick and safe needle removal in a simple procedure by the user. Cap means 20 having movable closure lid 21 provides engageable slot means 22 for secure holding of needle hub 12 during detachment. Slot means 22 is integrally formed with a plate means, disclosed as generally circular top plate 23, and opens to storage container 19. Slot means 22, in the mode disclosed, includes a notch means, preferably comprising three stepped notches 24a, 24b and 24c. Each stepped notch forms a gap provided to accommodate a particular needle hub size such that device 18 can be used with a variety of needles commonly encountered, particularly during daily hospital procedures. Entry to slot means 22 is made easily available through entry port means 25 forming a larger portion of slot means 22 so that the user can properly insert cannular needle 11 to extend into storage container 19 immediately after use. Then the syringe 10 with attached cannular needle 11 may be moved sideways for engagement with a stepped notch.

It will be clear that conventional hub 12 is initially threadably engaged within ferrule 13 by clockwise screw engagement. Accordingly, to unwind, or detach, hub 12 provision must be made for a counter-clockwise unwinding manipulation of syringe 10. This is achieved by the further provision of a series of integrally connected depending walls preferably extending downwardly from top plate 23 and forming a lower portion of slot means 22. Entry port means 25 includes depending circular wall 26 which terminates at first and second terminii, or wall ends, integrally with other wall structures. At one side, circular wall 26 terminates at long wall 27 forming one side of slot means 22 opposite step notches 24a, 24b and 24c. Long wall 27 is provided, in the example, tangent with circular wall 26. Entry port means 25 need not be limited to a circular opening and other shaped openings, large enough to accept needle hubs, are within the purview of the invention.

At another terminus, at a second end, circular wall 26 terminates at a side wall 28c of stepped notch 24c. Each notch includes a side wall, e.g. stepped notch 24a has sidewall 28a and stepped notch 24b has side wall 28b. To complete the continuous depending wall structure, front wall 29a integrally extends between long wall 27 to terminate at sidewall 28a. Similarly, front walls 29B and 29c interconnect sidewalls 28a to 28b, and 28b to 28c, respectively. Slot means 22 comprises a continuous wall structure depending below top plate 23. This offers positive engagement with a flange collar 14 during unthreading manipulation.

In a typical configuration, flange collar 14 has four flanges. To facilitate the counter-clockwise disengagement, one flange would contact and be restrained at a side wall 28a, 28b or 28c and another flange at long wall 27. During unwinding, these flanges would be stopped from rotating and held in place by a sidewall and long wall 27. The action would be similar to a wrench engaging a hex-nut where the jaws of the wrench would engage apices of the hexagon.

It will be understood that with conventional threading, the mirror-image of slot means 22 would not facilitate counter-clockwise unthreading, since flange collar 14 contacting long wall 27 would be urged away from the wall rather than into it to restrain it during detachment procedures. Stated another way, when looking in a direction downwardly at cap means 20, along long wall 27, stepped notches 24a, 24b and 24c would be to the left of long wall 27. Preferably, detachment, or removal, is accomplished by holding device 18 steady while turning syringe 10. However, device 18 could be rotated and syringe 10 held steady to achieve needle removal. If an unconventional left-handed screw threading were encountered, the mirror image configuration would, however, be required wherein slot means 22 then would be made to have stepped notches to the right of long wall 27.

While the gaps of the stepped notches, being the distances between side walls and long wall 27, can be varied, it is preferable to provide gap dimensions in correspondence with conventional needle hub collar sizes. For example, in the embodiment disclosed, stepped notch 24a provides a gap between sidewall 28a and long wall 27 of about 0.155 inches (3.94 mm). This dimension will accommodate medical multi-sampling needles, such as those manufactured by Becton-Dickinson Co. and Turumo Co., and Becton-Dickinson Co. Leur syringe needles. Stepped notch 24b provides a gap of about 0.206 inches (5.23 mm) for removal of, for example, Monoject Division of Sherwood Medical Co. multi-sampling needles; MPL, subsidiary of Affiliated Hospital Products Co., multi-sampling needles and Monoject Leur syringe needles. Stepped notch 24c is disclosed to have a gap of about 0.276 inches (7.01 mm) for utilization with Becton-Dickinson Co. and Turumo Medical Co. single sampling needles, among others.

It will be understood that the notch gaps may be manufactured as desired to fit other needle sizes. Also, slot means 22 may comprise a single notch, as well as a plurality. The shape of slot means 22 is not intended to be limited to the configuration disclosed and may be formed absent an entry port means 25, or without a depending wall portion. Stepped notches 28a, 28b and 28c are disclosed as being adjacent and having right-angle intersections of front walls with sidewalls. Such formation is preferred but other suitable configurations are envisioned, for example, separate, or independent notches could extend radially from an entry port means, like spokes of a wheel. Numerous other configurations will be apparent to those skilled in the art.

Because needle hubs are not so firmly engaged within syringe ferrules that a large amount of unthreading force is required, a close tolerance between notch means and needle hub is not mandatory and therefore a gap may be slightly larger than the minor dimension of a collar, but of a size such that during unwinding, one side, or flange, of a collar is in part restrained at a sidewall 28a-c, and another side of the collar contacts and is restrained at long wall 27. A flange collar 14 is shown, in phantom, in FIG. 3 in position for needle detachment within stepped notch 28c, where the notch gap is slightly larger than the minor dimension of collar 14 but contact at sidewall 28c and longwall 27 is yet afforded.

As unthreading is completed, cannular needle 11 may then be urged toward entry port means 25. As hub 12 disengages syringe 10, the needle 11 will drop into storage container 19, and will be safely removed without contact with the user. Base 15 could have substantially the same width as collar 14 and would be able to simply drop downward from a stepped notch without movement to entry port means 25. Then closure means, being movable closure lid 21, may be rotated by pushing manipulable means, being tabs 30, to position access aperture 31 of movable closure lid 21 away from slot means 22 to disposition over solid portions of top plate 23 and safely cover storage container 19. To facilitate rotational closure, movable closure lid 21 includes post 33 positioned in a freely rotational manner within pivot hole 32 of top plate 23.

When viewing FIG. 4 in conjunction with FIG. 5, it is apparent that open and close positioning means are provided by dimples 34 and raised portion 35. Dimples 34 are small recesses within movable closure lid 21 radially extending from post 33 in positional correspondence with raised portion 35 extending radially from pivot hole 32. In the preferred embodiment, there are three dimples 34. Two dimples 35 are located so that the movable closure lid 21 may be positioned to dispose access aperture 31 over solid portions of top plate 23 in a closed orientation. A third dimple 34 is in an open position which aligns access aperture 31 over slot means 22, to prepare for removal procedures. The provisions of dimples 34 and raised portions 35 allow the user to quickly select a desired position for movable closure lid 21.

Cap means 20 and storage container 19 preferably are formed from a resilient thermoplastic material manufactured by conventional vacu-forming or injection molding procedures. Thus raised portion 35 and dimples 34 offer resilient engagement and disengagement such that the user senses when engagement is attained for proper positioning.

While the examples in the Figures show storage container 19 to be cylindrical and cap means 20 circular, it is envisioned that a wide variety of shapes may be provided by injection molding and vacu-forming techniques. Movable closure means need not be limited to the circular disc-like formation for lid 21 and may also comprise different shapes, provided movement to closed and open positions with respect to slot means 22 is attained.

In the mode disclosed, cap means 20 is adhesively fastened to storage container 19. Raised rim lip 36 is formed integrally with top plate 23 and terminates in a downwardly disposed peripheral skirt 37. Movable closure lid 21 is movably positioned within the recess formed within the periphery of raised rim lip 36 to minimize accidental opening or closing contact. A bonding adhesive can be initially applied to skirt 37, container 19, or both. Proper positioning of cap means 20 is provided by stop 38 extending circumferentially about skirt 37 at a predetermined distance below raised rim lip 36 such that cap means 20 may be placed, prior to bonding, at the position where stop 38 contacts container 19 along an upper container rim edge. While a bonding adhesive is preferably utilized, ultrasonic bonding, which melts plastic and bonds skirt 37 with container 29 is another method that may be alternately used for successful fastening.

FIG. 4 provides an additional safety feature, in phantom, being alternate rim guard 39 which extends outwardly from skirt 37 preferably from a position otherwise coinciding with stop 38. Rim guard 39, so located, performs the dual functions of safety and positioning. It would be clear, however, that alternate rim guard 39 may extend outwardly from skirt 37 above stop 38, or could comprises an upper ring-like ledge extending from storage container 19 generally adjacent cap means 20 to provide an additional barrier between the needles being inserted into container 19 and the user's hand.

FIG. 6 shows one alternate embodiment for the invention and comprises removal and disposal device 18'. Cap means 40 includes closure means comprising movable lid 41, which is eccentrically located. Cap means 40 includes slot means 42 substantially identical to slot means 22 and having stepped notches 43. Movement for opening and closing the slot means 42 is afforded by lid 41 including a ridged edge 44 capable of rotational movement by the user's fingers. Access aperture 45 may be moved over or away from slot means 42 for opened or closed positioning. Post 46 is movably retained by eccentric pivot hole 47. The diameter of lid 41 is such that ridge 44 terminates generally adjacent skirt 48 of cap means 40, slightly inwardly thereof, such that accidental rotation is minimized between uses. The cap 40 and the container 49 in the device 18' are removably connected by a threaded engagement, rather than by a permanent bonded fastening. Accordingly, the cap skirt 48 is internally threaded for fixture to container 49 by engagement with the threads 50. In this embodiment cap means 40 includes the salient characterizing features of the invention but provides an alternative conformation for access to slot means 42 and removability of cap means from container 49, well within the scope of the invention. The ability to remove the cap means 40 allows an accumulation of needles to be emptied to a refuse container or the like, so that the device 18' could then be re-used. Removability could be afforded by numerous non-threaded means, such as, by way of examples, a snap-lip, or friction-fit, engagement between cap means and storage container.

Additionally, the embodiment shown for device 18, in FIGS. 1-5, could also be provided with removable cap means by means of a close tolerance friction-fit between storage container 19 and skirt 37. Further, skirt 37 may be formed to engage exterior sides of container 19 rather than inside, as would be clear. Such modifications and other alternate embodiments are intended to fall within the purview of the invention.

As described above, FIGS. 1-6 disclose embodiments using separate cap means and storage containers, which may be permanently fastened together, or which may include removable cap means. In contrast, FIG. 7 discloses a device 18" having an integral construction. Device 18" comprises cap means 51 and storage container 52 associated in a unitary formation. Thus, upon filling storage container 52 with detached needles, device 18" would be discarded. Cap means 51 includes slot means 53 having access thereto controlled by a closure means, such as closure lid 54, which includes a hinged pivot means rather than the previously described rotatable access aperture. Lid 54 in this embodiment is a solid plate-like member being pivotable at hinged pivot means 55. Hinged pivot means 55 is a necked down portion of lid 54. This arrangement permits lid 54 to cover cap means 51 and then to pivot upward, as shown in phantom, to allow access to slot means 53. Lid 54 is anchored by a bulb 56 engaging in a hole 57, but lid 54 may optionally be integrally formed with device 18". Lid 54 is preferably capable of resilient snap engagement, in the closed position, by means of the barb-end 58 snap-engaging notch 59 at a side opposite hinged pivot means 55. Pivoting movement to the closed or open position is made possible by the user grasping handle 60 to pivot lid 54 downward or upward.

Cap means 51 includes top plate 61 with slot means 53 opening therethrough into storage container 52. Top plate 61 is disclosed to have a thickness substantially corresponding to the depending dimension for the wall means of slot means 22 as shown in FIGS. 3 and 4 for device 18. It will be appreciated that with the thickened dimension for plate 61, slot means 53 has a corresponding wall depth and need not further include depending wall formations, such as the sidewalls, front walls and long wall of device 18, which extend below the relatively thinner top plate 23. This increased plate thickness serves the same function and purpose as described with respect to depending walls of slot means 22. It will also be understood that cap means 20 of device 18 and cap means 40 of device 18', may include a thicker plate means, whereby slot means therethrough would have a corresponding wall means depth not requiring further wall extensions above or below the plate means.

To allow for the accumulation of numerous used needles, the storage containers 19, 49 and 52 are provided with a diameter of about 2 inches (51 mm) and a height of about 3½ inches (89 mm). This preferred size ensures portability while providing the device with a capacity for used needles which allows medical personnel to move from patient to patient without having to empty the device, or obtain a new one, after only a few injections or samplings. A larger collection container could be provided for transportation on a cart or the like to achieve greater needle-handling capacity. Furthermore, a rim-like extension, similar to alternate rim guard 39, could be provided to extend outwardly adjacent the cap means such that a circular opening in a planar cart surface could be provided wherein the storage container could be disposed in the opening and supported by the upper rim-like extension at the cart surface.

The device in accordance with this invention allows for the quick and safe removal of used needles from a syringe, and facilitates their subsequent disposal. It has particular application for threaded hubs of cannular needles by allowing for rotational unthreading of the needles from a syringe, followed immediately by a disposition of the needles into a container which has closure means for safe containment. Needles which are friction-fit into ferrules of syringes are as well suited for use with the inventive device. With friction-fit needles the hub of the needle could be caught at wall means of the slot means, and the syringe could be pulled upwardly for removing and disposing of the used needle into the storage container. In achieving safety, the invention further provides economic needle disposal without rehandling, since the device is preferably formed from inexpensive materials, and may be discarded with the used needles safely contained therein. Accordingly, various alternatives of the invention are intended to fall within the scope of the invention, as set forth in the following claims.

What is claimed is:

1. A needle removal and disposal device for detaching single or double-ended sampling needles which are thread engaged to a syringe body and storing detached sampling needles, said device comprising:
   storage container means;
   cap means associated with said storage container means, said cap means having a plate means with slot means opening therethrough, said slot means including integral wall means depending into said storage container means, entry port means and a plurality of stepped notches each having a different gap dimension for accommodating different sized needle hub portions; and
   closure means pivotably associated with said plate means and being movable with respect to said slot means for controlling access thereto;
   wherein said device is capable of engaging a sampling needle hub portion at a stepped notch whereby a syringe thread-engaged to a hub portion may be rotated with respect to the hub portion for detachment of a sampling needle, whereby detached needles and hub portions may be deposited through said entry port means into said storage container means, said device providing said storage container means for accumulation of sampling needles subsequent to detachment from syringes, and whereby said pivotable closure means is capable of moving to close access to said slot means and provide safe storage of sampling needles within said storage container means.

2. A needle removal and disposal device as claimed in claim 1 wherein said closure means comprises a lid having finger manipulable means to effect movement with respect to said slot means.

3. A needle removal and disposal device as claimed in claim 3 wherein said movable lid includes an access aperture therethrough being movable with respect to said slot means.

4. A needle removal and disposal device as claimed in claim 3 wherein said movable lid and plate means include resilient positioning means resiliently engageable at predetermined positions of said movable lid with respect to said slot means.

5. A needle removal and disposal device as claimed in claim 1 wherein said plate means includes a continuous peripheral raised lip means extending therefrom to form a recess accommodating said closure means therein.

6. A needle removal and disposal device as claimed in claim 1 wherein said cap means is permanently fastened to said storage container means.

7. A needle removal and disposal device as claimed in claim 1 wherein said cap means is removably fastened to said storage container means.

8. A needle removal and disposal device as claimed in claim 1 wherein said cap means and storage container means are integrally formed.

9. A needle removal and disposal device as claimed in claim 1 wherein said device includes rim guard means extending outwardly thereof in adjacent promixity with said cap means.

10. A needle removal and disposal device for use with single or double-ended sampling needles having hub portions thread-engaging a syringe at the hub portion, said device comprising:
    cap means having a plate means with slot means opening therethrough, said slot means including entry port means and a plurality of stepped notches, each notch having a different notch gap dimension permitting engagement with different sized needle hub portions, said slot means further including depending wall means integral with said plate means,
    movable closure means pivotably associating with said cap means at pivot means thereof, said movable closure means being selectively movable between an open access and closed access position with respect to said slot means,
    storage container means, associating with said cap means, said slot means opening to said storage container means, and said wall means depending into said storage container means,
wherein said device facilitates detaching a sampling needle from a syringe by engagement of a needle hub portion at a stepped notch and rotation of the syringe with respect to said sampling needle hub portion, whereby a detached sampling needle and associated hub portion may be deposited through said entry port means for storage within said storage container means therebelow.

11. A needle removal and disposal device as claimed in claim 10 wherein said cap means and storage container means are permanently fastened together.

12. A needle removal and disposal device as claimed in claim 11 wherein said cap means and storage container means are permanently fastened by adhesive bonding.

13. A needle removal and disposal device as claimed in claim 11 wherein said cap means and storage container means are permanently fastened by ultrasonic bonding.

14. A needle removal and disposal device as claimed in claim 10 wherein said cap means and storage container means are removably fastened.

15. A needle removal and disposal device as claimed in claim 14 wherein said removable fastening comprises thread engagement means.

16. A needle removal and disposal device as claimed in claim 10 wherein said cap means and storage container means comprise an integrally formed unitary construction.

17. A needle removal and disposal device as claimed in claim 16 wherein said movable closure means is integrally formed with said cap means.

18. A needle removal and disposal device as claimed in claim 10 wherein said device includes rim guard means extending outwardly thereof adjacent upper portions of said storage container.

* * * * *